United States Patent
Biedermann et al.

(10) Patent No.: US 8,764,805 B2
(45) Date of Patent: Jul. 1, 2014

(54) STABILIZATION DEVICE FOR STABILIZING VERTEBRAE OR BONE PARTS

(75) Inventors: Lutz Biedermann, VS-Villingen (DE);
Wilfried Matthis, Weisweil (DE);
Berthold Dannecker, St. Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 55 days.

(21) Appl. No.: 13/336,693

(22) Filed: Dec. 23, 2011

(65) Prior Publication Data

US 2012/0165874 A1  Jun. 28, 2012

Related U.S. Application Data

(60) Provisional application No. 61/426,757, filed on Dec. 23, 2010.

(30) Foreign Application Priority Data

Dec. 23, 2010  (EP) .................................. 10196866

(51) Int. Cl.
*A61B 17/70* (2006.01)

(52) U.S. Cl.
USPC ......................... 606/278; 606/269; 606/272

(58) Field of Classification Search
USPC ........................ 606/250–279, 86 A
See application file for complete search history.

(56) References Cited

U.S. PATENT DOCUMENTS

| 5,873,878 | A  | 2/1999  | Harms et al. |
| 6,077,262 | A  | 6/2000  | Schläpfer et al. |
| 7,857,834 | B2 | 12/2010 | Boschert |
| 8,257,399 | B2 | 9/2012  | Biedermann et al. |
| 2005/0261687 | A1 | 11/2005 | Garamszegi et al. |
| 2007/0083199 | A1* | 4/2007 | Baccelli ........................ 606/61 |
| 2007/0161999 | A1* | 7/2007 | Biedermann et al. .......... 606/61 |

FOREIGN PATENT DOCUMENTS

| DE | 41 10 002 C1  | 5/1992 |
| DE | 199 12 364 A1 | 10/2009 |
| EP | 2 070 485 A1  | 6/2009 |
| EP | 2 201 903 A1  | 6/2010 |

OTHER PUBLICATIONS

European Search Report for European Application No. EP 10 19 6866, European Search report dated Mar. 23, 2011 (6 pgs.).
U.S. Office action dated Feb. 7, 2011, for U.S. Appl. No. 12/333,873 (9 pages).

* cited by examiner

*Primary Examiner* — Mary Hoffman
*Assistant Examiner* — Tara Carter
(74) *Attorney, Agent, or Firm* — Christie, Parker & Hale, LLP

(57) ABSTRACT

A stabilization assembly for stabilizing a vertebra or other bone includes: at least two rods having different diameters; an anchoring element having a shaft and a head; a receiving part for interchangeably receiving any one of the rods to connect the rod to the anchoring element, the receiving part including a rod receiving portion with a channel for receiving the rod, and a head receiving portion having an open end and being flexible to allow introduction and clamping of the head; and a locking ring configured to be arranged around the head receiving portion and to clamp the head in the head receiving portion; wherein the locking ring includes a contact surface configured to contact any one of the at least two rods at at least two distinct contact areas that are spaced apart from one another in a circumferential direction of the rod.

15 Claims, 6 Drawing Sheets

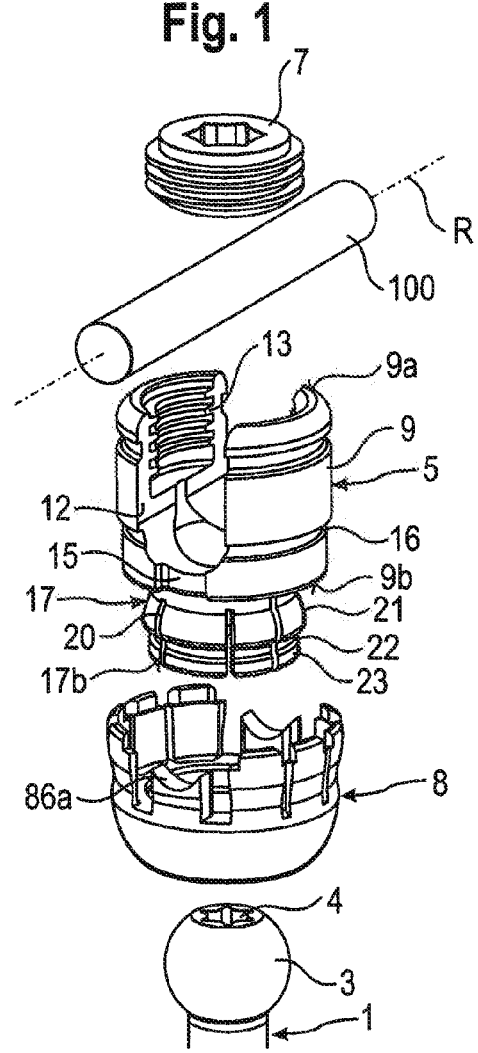
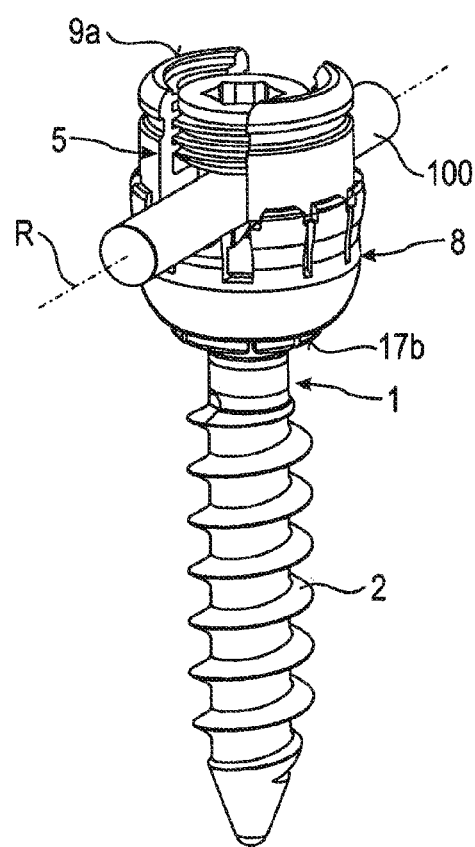

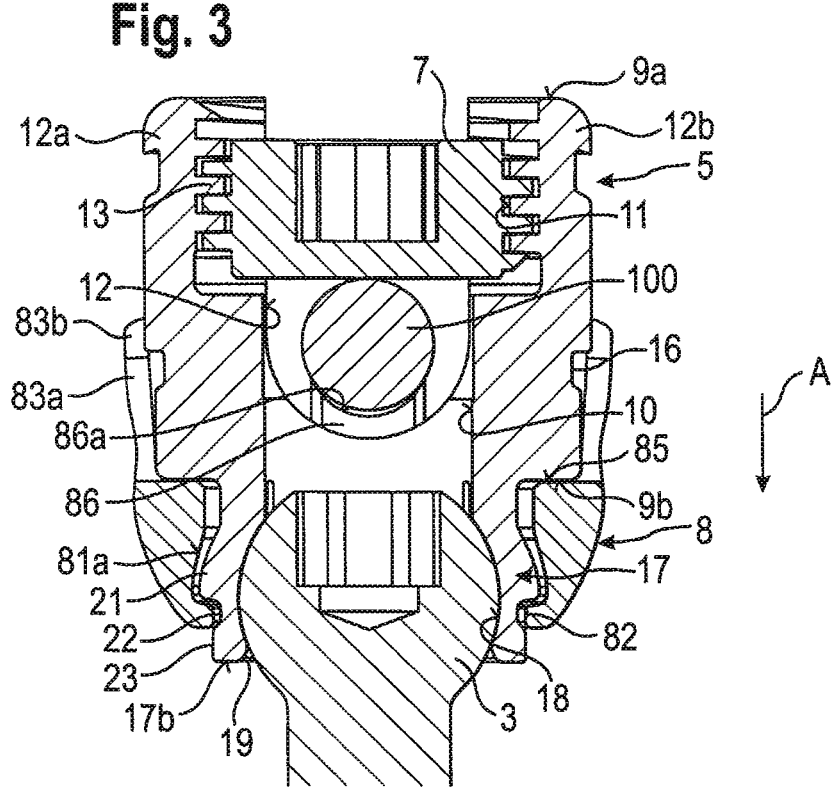
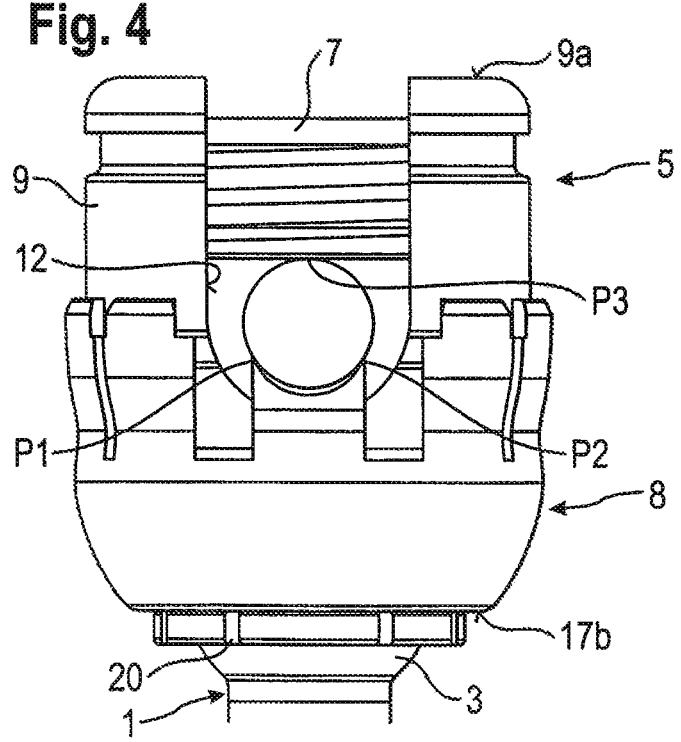

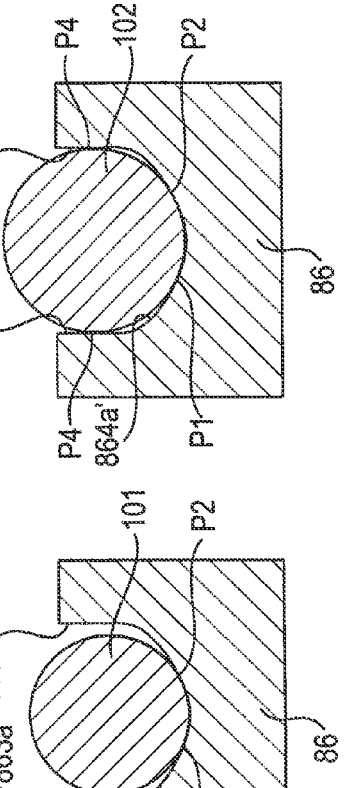
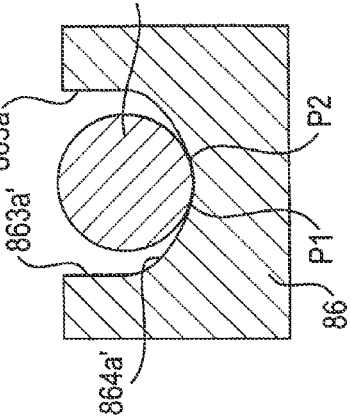

STABILIZATION DEVICE FOR STABILIZING VERTEBRAE OR BONE PARTS

CROSS-REFERENCE TO RELATED APPLICATIONS

The present application claims the benefit of U.S. Provisional Patent Application Ser. No. 61/426,757, filed Dec. 23, 2010, the contents of which are hereby incorporated by reference in its entirety, and claims priority to European Patent Application EP 1.0 196 866.7, filed Dec. 23, 2010, the contents of which are hereby incorporated by reference in its entirety.

BACKGROUND

1. Field of the Invention

The invention relates to a stabilization device for stabilizing vertebrae or bones that includes a bone anchoring device and at least two stabilization rods having different diameters.

2. Description of Related Art

For stabilizing the spinal column, bone anchoring devices are known that include a shaft to be anchored in bone and a head to be connected to a rod. Usually, a rod connects several bone anchoring devices. Depending on the medical condition and the region of the spine that is to be stabilized, rods with different diameters may be required. The diameters of the rods range from 3 mm to more than 6 mm. Generally, the diameter of the rods used in the lower part of the spine is larger than the diameter of the rods used in the upper part of the spine. For example, in the cervical-thoracic region of the spine, rods with a diameter of 3 mm to 3.5 mm may be used, in the transitional zones between the cervical-thoracic and the thoracic-lumbar region, rods with a diameter of 3.5 mm to 4.5 mm may be used, in the thoracic-lumbar region, rods of usually 4.5 mm to 5.5 mm may be used, and in the lumbar-sacral region, rods with a diameter of 5 mm to 6.35 mm may be utilized.

For each rod of a certain diameter, specific bone anchoring devices, such as pedicle screws, are required. They differ from each other in particular by the size of the recess into which the rod is inserted. The need for these different bone anchoring devices increases costs and renders spinal surgery more complicated for a surgeon or practitioner.

U.S. Pat. No. 5,873,878 discloses an anchoring member for attachment to a vertebra and for use with a first rod having a first diameter and a second rod having a second, smaller diameter. The anchoring member includes an insert member which can be inserted into the head of the anchoring member so as to allow the insertion of a rod with a smaller diameter.

EP 2 070 485 A1 describes a monoaxial bone anchoring device and a polyaxial bone anchoring device each of which can be used with rods of different diameters.

SUMMARY

It is an object of the invention to provide a stabilization device for vertebrae or other bones that is further improved with respect to system modularity.

With a stabilization device according to embodiments of the invention, a modular system can be provided that allows combining of various anchoring elements with any suitable receiving part and any suitable rod, on demand, depending on the actual clinical requirements. This reduces costs associated with polyaxial screws, reduces inventory, and gives the surgeon a more substantial choice of implants.

The assembly of the stabilization device according to embodiments of the invention can be carried out by any specialist, for example, by a surgeon or any personnel assisting him before or during surgery.

The embodiments of the anchoring device have an advantage in that they provide a safe clamping of any of a number of rods having different diameters. The clamping force does not depend on the diameter of the rod used. Also, the clamping of rods of different diameters can be achieved in a stepless manner.

Furthermore, embodiments of the bone anchoring device are constructed to reduce or minimize the number of parts. Hence, the fixation of different sized rods does not require additional parts.

Embodiments of the stabilization device can be used, for example, for the correction of scoliosis in children. When a child is diagnosed with scoliosis, it may be necessary to employ an adjustable scoliosis correction device. For example, as the child grows up it may be necessary to use other rods with a greater diameter than those originally inserted. With the stabilization device according to embodiments of the invention, it is possible to replace the originally used rods in a second surgery with the bone anchors already anchored in the vertebrae.

BRIEF DESCRIPTION OF THE DRAWINGS

Further features and advantages of the invention will become apparent from the description of embodiments by means of the accompanying drawings. In the drawings:

FIG. 1 shows a perspective exploded view of a stabilization device with a first rod according to a first embodiment;

FIG. 2 shows a perspective view of the stabilization device of FIG. 1 in an assembled state;

FIG. 3 shows a cross-sectional view of the stabilization device of FIG. 2 with the first rod in an assembled state, the section being taken perpendicular to a rod axis;

FIG. 4 shows a side view of the stabilization device of FIG. 3;

FIG. 14a to 14c show enlarged cross-sectional views of a portion of a rod support of a locking ring according to a further modified embodiment, with rods having different diameters; and FIGS. 15a to 15c show enlarged cross-sectional views of portion of a rod support of a locking ring according to another further modified embodiment, with rods having different diameters.

DETAILED DESCRIPTION

Figure 5:
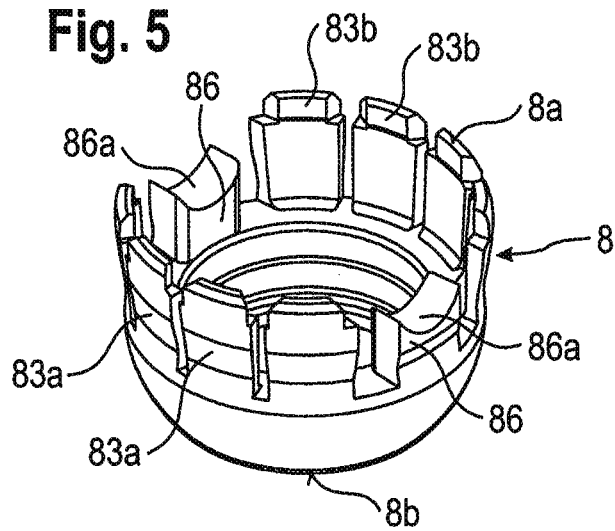
FIG. 5 shows a perspective view of a locking ring of the stabilization device according to FIGS. 1 to 4.
Figure 6:
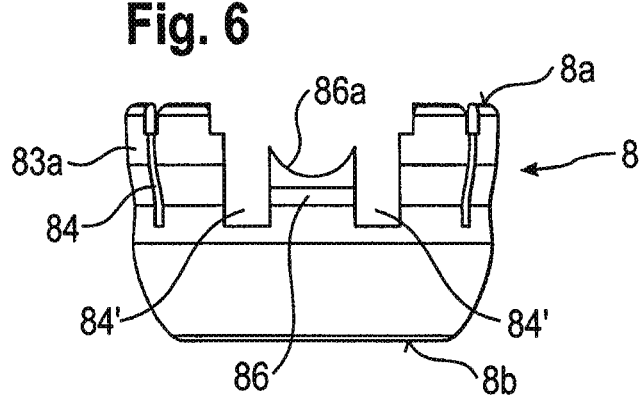
FIG. 6 shows a side view of the locking ring of FIG. 5.
Figure 7:
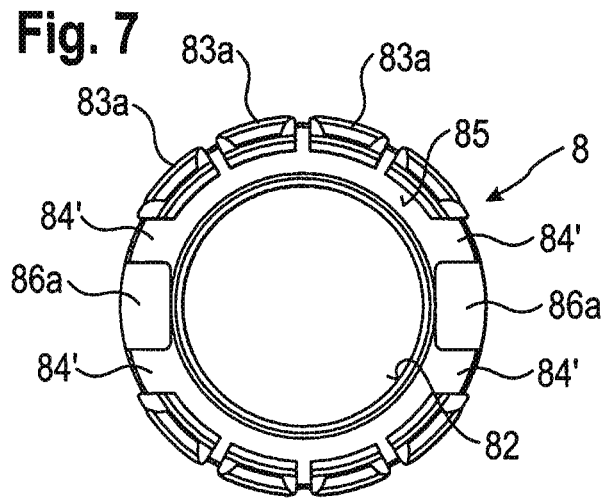
FIG. 7 shows a top view of the locking ring of FIG. 5.

As shown in FIGS. 1 and 2, a stabilization device according to a first embodiment includes a bone anchoring element 1 in the form of a bone screw having a threaded shaft 2 and a head 3 with a curved surface portion. In this embodiment, the head 3 is spherical segment-shaped. The head 3 has a recess 4 for engagement with a tool. The stabilization device also includes a receiving part 5 for receiving a first rod 100 to connect the first rod 100 to the bone anchoring element 1. Further, a fixation element 7, in the form of an inner screw in this embodiment, is provided for fixing the rod 100 in the receiving part 5. The stabilization device also includes a locking ring 8 for locking the head 3 in the receiving part 5. At least one further rod (not shown) is provided that has a diameter different from a diameter of the first rod 100. The rods may have circular cross-sections. Also, the rods may have substantially smooth surfaces.

Figure 8:
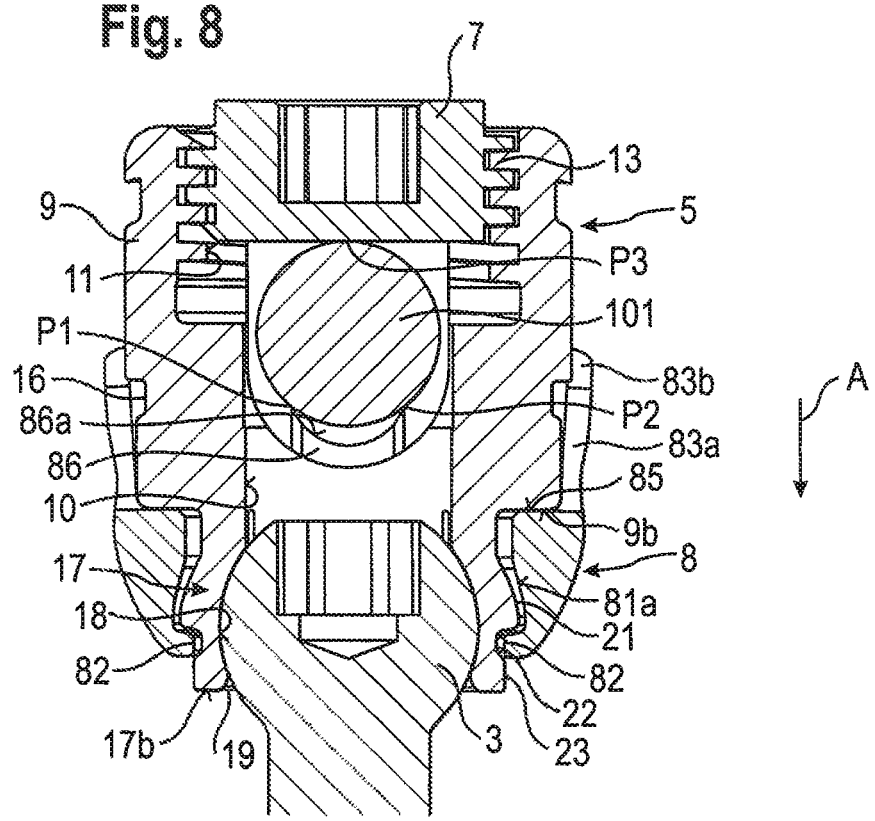
FIG. 8 shows a cross-sectional view of the stabilization device of FIG. 2 with a second rod in a assembled state, the section being taken perpendicular to the rod axis.

The receiving part 5 will be explained with reference to FIGS. 1 to 4. The receiving part 5 includes a rod receiving portion 9, which is substantially cylindrical and which has a first end 9a and an opposite second end 9b. A coaxial first bore 10 is provided at the second end 9b as shown in FIGS. 3 and 8. A diameter of the first bore 10 is smaller than a diameter of the head 3 of the bone anchoring element 1. The rod receiving portion 9 further has a coaxial second bore 11 extending from the first end 9a to a distance from the second end 9b. A diameter of the second bore 11 is larger than a diameter of the first bore 10. A substantially U-shaped recess 12 extends from the first end 9a in a direction of the second end 9b in the rod receiving portion 9, the diameter of the recess 12 being larger than the diameter of any rod intended to be used with the stabilization device, so that the rod 100, or any other rod of the stabilization device, can be placed in the recess 12 and can be guided therein. By means of the recess 12, two free legs 12a, 12b are formed on which an internal thread 13 is provided. The internal thread 13 can be a metric thread, a flat thread, a negative angle thread, a saw-tooth thread, or can be any other thread form. Preferably, a thread form such as a flat thread or a negative angle thread is used, which prevents splaying of the legs 12a, 12b when the inner screw 7 is screwed in. A depth of the recess 12 is such that the rod 100, or any other rod of the stabilization device, and the inner screw 7 can be inserted between the legs 12a, 12b.

As can be seen in FIG. 1, cutouts 15 are provided in the rod receiving portion 9 on either end of a channel formed by the recess 12.

On an outer surface of the rod receiving portion 9, a groove 16 is provided which extends in a circumferential direction and serves for engagement with a portion of the locking ring 8.

At a side of the second end 9b, the receiving part 5 includes a head receiving portion 17 providing an accommodation space for the head 3 of the bone anchoring element 1. The head receiving portion 17 has a greatest outer diameter which is smaller than a greatest outer diameter of the rod receiving portion 9. An internal hollow section 18 forms a seat for the head 3 of the bone anchoring element 1 and is open via an opening 19 at a free end 17b of the head receiving portion 17. The hollow section 18 is adapted in its shape to the shape of the head 3, which in the embodiment shown is a spherical section to accommodate the spherical head 3. Furthermore, the hollow section 18 is configured to encompass the head 3 of the bone anchoring element 1 from the side, covering at least a region including the largest diameter of the head 3.

A plurality of slits 20 are provided in the head receiving portion 17 which are open to the free end 17b. The slits 20 render the head receiving portion 17 flexible so that the head receiving portion 17 can be compressed to clamp and finally lock the head 3 in the hollow internal portion 18 by means of friction. A number and size of the slits 20 is provided depending on the desired flexibility of the head receiving portion 17. The flexibility of the head receiving portion 17 is configured such that the head 3 of the bone anchoring element 1 can be inserted by expanding the head receiving portion 17, and can be clamped by compressing the head receiving portion 17.

An outer surface of the head receiving portion 17 has a first portion 21 with an outer diameter which increases towards free end 17b, for example in an outwardly curved manner. Adjacent to the first portion 21, there is a circumferential groove 22 which is recessed with respect to the first portion 21 and which serves for engagement with a portion of the locking ring 8. Adjacent to the groove 22 on a side opposite the first portion 21, there is a third portion 23 of the head receiving portion 17 with a substantially cylindrical outer surface. The third portion 23 is configured to cooperate with a portion of the locking ring 8 to enhance the clamping effect of the locking ring 8.

The locking ring 8 will now be described with reference to FIGS. 1 to 7. The locking ring 8 is substantially cylindrical and has an upper end 8a and a lower end 8b. In a mounted state, the upper end 8a is oriented in the direction of the first end 9a of the rod receiving portion 9, and the lower end 8b is oriented towards the free end 17b of the head receiving portion 17. As can be seen in FIGS. 3 and 8, an inner surface portion 81a is provided near the upper end 8a which cooperates with the first outer surface portion 21 of the head receiving portion 17 to exert a compression force onto the head receiving portion 17.

At the lower end 8b, the locking ring includes an inwardly projecting edge 82, an inner diameter of which is smaller than an inner diameter of the other portions of the locking ring 8. The inwardly projecting edge 82 can be positioned to engage or be adjacent to the groove 22 of the head receiving portion 17.

The locking ring 8 further has upwardly extending wall portions 83a, which are separated from each other by slits 84. The upwardly extending wall portions 83a are arranged at an outer circumference of an inner circumferential shoulder 85 of the locking ring 8, and render an upper portion of the locking ring 8 flexible. A number and size of the slits 84 and a thickness of the wall portions 83a are configured such that a desired flexibility is obtained. At a free end, the wall portions 83a include engagement sections 83b which are shaped so as to engage the groove 16 provided on the outer surface of the rod receiving portion 9.

The locking ring 8 is sized in such a way with respect to the head receiving portion 17 that the head receiving portion 17 can expand within the locking ring 8 to allow for introduction of the head 3 when the locking ring 8 is in a first position relative to the receiving part 5, as shown in FIG. 3.

Two projections 86, which are located diametrically opposite to each other, are formed in an upper portion of the locking ring 8. The projections 86 have a height such that they extend into the cutouts 15 and project above the bottom of the substantially U-shaped recess 12, when the locking ring 8 is in a position in which the head 3 is not yet locked, for example, as shown in FIGS. 2-4. The projections 86 are separated from the upwardly extending wall portions 83a by slits 84', the sizes of which are designed such that a distance between the wall portions 83a to the left and right of the projections 86 is greater than a width of the cutouts 15 in the receiving part 5. The locking ring 8 is arranged in such a manner around the head receiving portion 17 of the receiving part 5 that the projections 86 are located at the positions of the recess 12 and the cutouts 15. By means of this, the projections 86 prevent the locking ring 8 from rotating relative to the receiving part 5 when the rod 100 is not inserted.

As can be seen in particular in FIGS. 3 to 6, a free end surface 86a of the projections 86 is concave. In the first embodiment, the free end surface 86a is formed as a cylindrical recess, with a cylinder radius that is smaller than a radius of the first rod 100 and smaller than the radius of any of the further rods intended to be used with the stabilization device, A width of the projections 86 in the region of the free end surface 86a is smaller than the diameter of any of the rods that are configured to be inserted. Hence, when the first rod 100 is inserted into the U-shaped recess 12 and placed onto the projections 86, the first rod 100 contacts the free end surface 86a of the projections 86 at two contact areas P1, P2, as seen for example, in FIG. 4, that are substantially formed as line contacts extending in the direction of the rod axis R.

The contact areas P1, P2 may be located slightly apart from free edges of the end surfaces 86a, towards a bottom or center of the free end surfaces 86a.

When the inner screw 7 is inserted and tightened, it contacts the rod 100 along a third contact area P3 that is on a top of the rod 100, as seen for example, in FIG. 4. The third contact area P3 is also substantially a line contact, which extends in the direction of the rod axis R.

The flexibility of the head receiving portion 17 and the size of the head receiving portion 17 at the open end 17b allows for mounting of the locking ring 8 by assembling the locking ring 8 from the free end 17b onto the head receiving portion 17.

The inner screw 7 has a thread corresponding to the internal thread 13. If a thread form which prevents or reduces the legs from splaying is used, a single fixation element such as the inner screw 7 is sufficient. This reduces the size of the bone anchoring device in a radial direction. In some embodiment, other fixation elements such as, for example an outer nut, are also possible.

Figure 9:
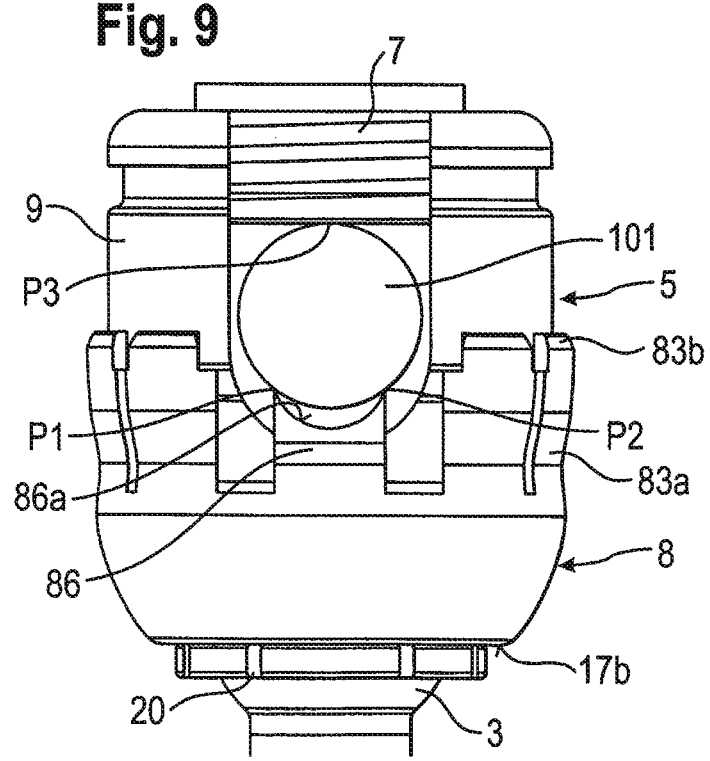
FIG. 9 shows a side view of the stabilization device of FIG. 8.

The stabilization device includes at least a second rod 101 which has a diameter that is greater than the diameter of the first rod 100, as shown in FIGS. 8 and 9. When the second rod 101 is inserted into the receiving part, the second rod 101 rests on the free edges of the end surfaces 86a of the projections 86 of the locking ring 8. Hence, contact areas P1 and P2 corresponding to the second rod 101 may be slightly farther apart from each other when compared to the contact areas corresponding to the first rod 100.

The dimensions of the projections 86, the concave free end surface 86a, and the diameter of the rods 100, 101, as well as the length and shape of the inner screw 7, are such that the rods 100, 101 are clamped along three contact lines P1, P2 and P3. An inserted rod is in a stable position when it is clamped in this way, similar to a three-point fixation. By means of this, a secure multi-line contact along the inserted rod is achieved at each projection 86. It should be understood that the contact lines are not infinitesimally thin lines, but are lines which have a certain thickness according to the contact between the respective parts that is macroscopically generated. Hence, a safe fixation independent of the diameter of the inserted rod is provided.

The diameter of the rods that can be used with the anchoring device may vary between a largest diameter and a smallest diameter that are defined geometrically in such a way that the rod has, in any case, two lines of contact with the free end surface 86a of the projections 86.

A second embodiment of the stabilization device differs from the first embodiment in the shape of the projections provided on the locking ring 8. All other portions of the stabilization device are the same or similar, and have the same reference numerals, while their descriptions are not repeated.

Figure 10:
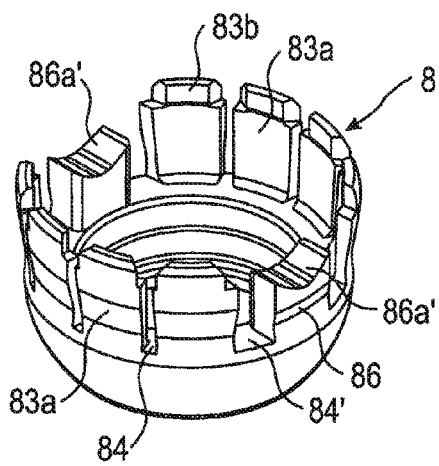
FIG. 10 shows a perspective view of a locking ring of a the stabilization device according to a second embodiment.
Figure 11:
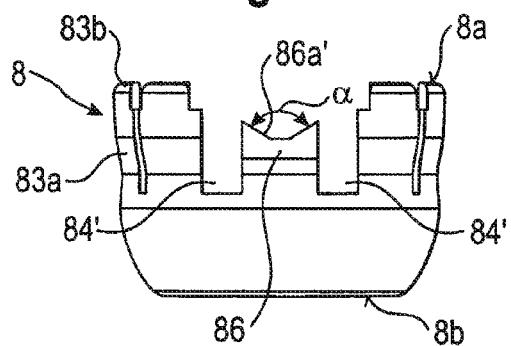
FIG. 11 shows a side view of the locking ring of FIG. 10.
Figure 12:
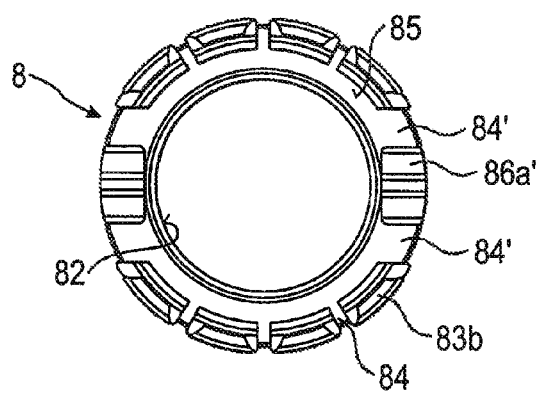
FIG. 12 shows a top view of the locking ring of FIG. 10.

As shown in FIGS. 10 to 12, the free end surfaces 86a' of the projections 86 according to the second embodiment form grooves having substantially V-shaped cross-sections. A bottom of the V-shape can be straight or rounded. An angle α formed by the V-shape is such that a rod with a diameter that is smaller than a largest diameter of the V-shaped groove contacts the groove at two opposite contact areas P1, P2 extending in a direction parallel to the rod axis R. As in the first embodiment, the contact areas are substantially line contacts.

Figure 13:
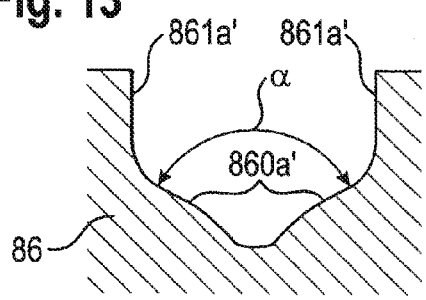
FIG. 13 shows an enlarged cross-sectional view of a portion of a rod support of a locking ring according a modified second embodiment.

As shown in FIG. 13, in a modified second embodiment, a bottom of the V-shaped groove has inwardly curved portions 860a' and straight sidewalls 861a'.

In a further modification, as shown in FIGS. 14a to 14c, a V-shaped groove additionally includes straight side walls 863a'.

In another further modification as shown in FIGS. 15a to 15c, a V-shaped groove has concavely curved sidewalls 864a' of the V-shape, and straight sidewalls 863a'. In the modified embodiments, an inserted rod can also rest on the free end surface 86a' along two contact areas P1, P2.

FIGS. 14a to 14c and FIGS. 15a to 15c schematically show contacts formed by various rods 100, 101, 102 with increasing diameter. The rods in each case rest in the V-shaped groove on two cross-sectional points, or when seen three-dimensionally, along two contact areas P1, P2 in the form of line contacts. From above, the rods may be clamped by the inner screw 7. Hence, each rod can be in a stable clamping position similar to a three-point clamping. If a large rod is used, for example, rod 102, the rod may touch the V-shaped groove also in regions of the straight side walls 863a' at contact areas P4.

The receiving part 5, the locking ring 8, the inner screw 7, and the bone anchoring element 1 may be made of a bio-compatible material, for example, of titanium or stainless steel, of a bio-compatible alloy such as Nitinol, or of a bio-compatible plastic material, such as polyether ether ketone (PEEK). The various parts can be made of the same or of different materials.

The function or operation of the stabilization device with the locking ring 8 will now be explained with referenced FIGS. 3 and 8. As shown in FIGS. 3 and 8, a first position of the locking 8, which is an insertion position and in which the locking ring 8 is latched with respect to the receiving part 5, is defined in such a way that the inwardly projecting edge 82 engages or is adjacent to groove 22 at the outer surface of the head receiving portion 17. The inner diameter of the inwardly projecting edge 82 is larger than the outer diameter of the head receiving portion 17 at the position of the groove 22, so as to allow an expansion of the head receiving portion 17 when the head 3 of the bone anchoring element 1 is introduced. In the first position, the locking ring 8 may additionally be held by a clamping force between the rod receiving portion 9 of the receiving part 5 and the flexible wall portions 83a of the locking ring 8, which may be bent slightly outwards.

When the locking ring 8 is in the first position, the head receiving portion 17 is not compressed. In this position, the introduction of the head 3 is possible. In the first position, the locking ring 8 is prevented from moving further upwards towards the first end 9a of the rod receiving portion 9, since the locking ring 8 abuts with the shoulder 85 against the second end 9b of the rod receiving portion 9, and in some embodiments with the inwardly projecting edge 82 against an upper wall of groove 22. The abutment of the locking ring 8 against the second end 9b holds the locking ring 8 in place, preventing further upward movement. Since portions of the inner diameter of the locking ring 8 are larger than corresponding portions of the outer diameter of the head receiving portion 17 in a non-compressed state, an expansion of the head receiving portion 17 into the spaces between the head receiving portion 17 and the locking ring 8 is possible. In this first position, an inserted head 3 can also freely pivot.

A second position (not shown), in which the locking ring 8 is latched with respect to the receiving part 5 and which is a pre-locking position, is achieved by shifting the locking ring 8 in a direction indicated by the arrow A towards the free end 17b of the head receiving portion 17, until the engagement portions 83b of the flexible wall portions 83a resiliently snap into the groove 16 provided at the rod receiving portion 9.

In the second position, the inner inclined surface 81a of the locking ring 8 presses against the first outer surface portion 21 of the head receiving portion 17, so as to compress the head receiving portion 17 to clamp the head 3 within the hollow internal portion 18, without fully locking the head 3 therein. In addition, the inwardly projecting edge 82 may press against the third portion 23 of the head receiving portion 17, resulting in an additional clamping force. Thereby, clamping of the head 3 can be effected not only from forces above or from the side of the head 3, but also from a region of the lower portion of or below the head 3. Under conditions arising during surgery, an angular position of the bone anchoring element 1 with respect to the receiving part 5 may be maintained, and can be loosened only by exerting an additional force onto the receiving part 5 or the bone anchoring element 1 when the locking ring 8 is in the pre-locking position. In this pre-locking position, the bone anchoring element 1 cannot be removed, from the receiving part 5, but angulation of the bone anchoring element 1 is still possible.

A third position (also not shown), which is a locking position, is achieved by shifting the locking ring 8 further downwards until the head 3 is finally locked within the head receiving portion 17. The inner surface 81a of the locking ring 8 engages the outer surface of the first portion 21 of the head receiving portion 17 in such a way that the head 3 is locked by further compression of the head receiving portion 17. In addition, the inwardly projecting edge 82 further compresses the head receiving portion 17 at the lower portion 23, thereby enhancing a locking force.

The bone anchoring device may be preassembled as follows. First, the locking ring 8 is mounted onto the receiving part 5 from the free end 17b. This can be done, for example, by the manufacturer. Preferably, the locking ring 8 is initially in the first position, as shown in FIGS. 3 an 8, in which the locking ring 8 is latched, for example, by engagement of the inwardly projecting edge 82 with the groove 22. Thereafter, the head 3 of the bone anchoring element 1 is introduced from the free end 17b into the hollow internal portion 18 of the head receiving portion 17. Thereafter, the locking ring 8 is moved downwards relative to the receiving part (e.g., along direction A in FIG. 3), so that the inwardly projecting edge 82 slides out of the groove 22 and the engagement portions 83b of the flexible wall portions 83a snap into groove 16, where the locking ring 8 assumes the second position.

In use, during surgery, a preassembled bone anchoring device including the receiving part 5, the bone anchoring element 1, and the locking ring 8, which may be in the pre-locking position, is screwed into a bone. The recess 4 of the head 3 can be accessed with a screw tool through the first bore 10.

A rod that has a diameter suitable for the specific clinical application is selected and inserted into the recess 12 until the rod is supported by the free end surfaces 86a of the projections 86. Hence, with the stabilization device according to embodiments of the invention, a modular system is provided that allows a user to select and assemble a suitable bone anchoring element and a suitable rod to be used with a particular receiving part.

To correctly align the receiving part 5 with respect to the rod, the receiving part 5 may be pivoted. Once a correct position of the bone anchoring devices relative to the rod is achieved, the inner screw 7 is tightened for each bone anchoring device. Since the rod abuts onto the projections 86 of the locking rings 8, the locking rings 8 are shifted downward into the third position, which is the locking position. When the locking rings 8 are moved towards the free end 17b of the head receiving portion 17 to the locking position, the locking rings 8 compress the head receiving portion 17, thereby locking the head 3. Final tightening of the inner screws 7 may lock the rod and the heads 3 simultaneously relative to the respective receiving parts 5.

Further modifications of the embodiments described are also possible. For example, the locking ring can have various other shapes. The pre-locking function can also be realized in various other manners.

For the bone anchoring element, various different kinds of known bone anchoring elements, such as screws, nails, hooks, cannulated screws, and/or bone anchoring elements with separable heads and shafts, among others, can be used.

The rods utilized may also have a curvature along the rod axis.

In some embodiments, the head receiving portion can have an inclined open end, or can be otherwise asymmetric to allow for a greater angulation of the head in one direction.

In addition, the outer surface of the head receiving portion and the inner surface of the locking ring can have various other shapes which allow for compression of the head receiving portion when the locking ring is shifted downwards, as described above.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A stabilization assembly for stabilizing a vertebra or other bone, comprising:
    at least two rods having different diameters;
    an anchoring element having a shaft for anchoring in a bone and a head;
    a receiving part for interchangeably receiving any one of the at least two rods to connect the rod to the anchoring element, the receiving part comprising a rod receiving portion with a channel for receiving the rod, and a head receiving portion for accommodating the head of the anchoring element, the head receiving portion having an open end and being flexible to allow introduction and clamping of the head; and
    a locking ring configured to be arranged around the head receiving portion and to clamp the head in the head receiving portion, wherein the locking ring can assume a first position around the head receiving portion where the head can be introduced into the head receiving portion, and a second position closer to the open end of the head receiving portion where the head is clamped in the head receiving portion by the locking ring;
    wherein the locking ring comprises a contact surface configured to contact any one of the at least two rods at at least two distinct contact areas that are spaced apart from one another in a circumferential direction of the rod, and wherein when any one of the at least two rods is in contact with the contact surface, the contact areas are separated in the circumferential direction by a region in which the rod and the contact surface are spaced apart.

2. The stabilization assembly of claim 1, wherein the contact surface is shaped such that when the contact surface is in contact with any one of the at least two rods, the contact areas extend along a rod axis.

3. The stabilization assembly of claim 1, wherein the contact surface is curved with a radius of curvature smaller than a radius of each of the at least two rods.

4. The stabilization assembly of claim 1, wherein the contact surface is defined by a cylindrical recess with a diameter smaller than a diameter of each of the at least two rods.

5. The stabilization assembly of claim 1, wherein the contact surface is defined by a substantially V-shaped portion.

6. The stabilization assembly of claim 5, wherein each side wall of a base forming the V-shape is curved.

7. The stabilization assembly of claim 5, wherein the contact surface is further defined by straight sidewalls extending from the substantially V-shaped portion.

8. The stabilization assembly of claim 1, wherein the contact surface is configured to clamp each of the at least two rods in a stepless manner.

9. The stabilization assembly of claim 1, wherein at least one of the at least two rods has a substantially circular cross section.

10. The stabilization assembly of claim 1, wherein the locking ring comprises two projections that are offset by 180° from each other, and wherein a respective contact surface is located on each of the projections.

11. The stabilization assembly of claim 10, wherein the projections are configured to extend into the channel of the rod receiving portion.

12. The stabilization assembly of claim 1, wherein the locking ring is configured to be moved from the first position to the second position via pressure from the rod.

13. A method for stabilizing a vertebra or other bone with a stabilization assembly comprising at least two rods having different diameters, an anchoring element having a shaft for anchoring in a bone and a head, a receiving part for interchangeably receiving any one of the at least two rods to connect the rod to the anchoring element, the receiving part comprising a rod receiving portion with a channel for receiving the rod, and a head receiving portion for accommodating the head of the anchoring element and having an open end and being flexible to allow introduction and clamping of the head, and a locking ring configured to be arranged around the head receiving portion and to clamp the head in the head receiving portion, wherein the locking ring comprises a contact surface configured to contact any one of the at least two rods at at least two distinct contact areas that are spaced apart from one another in a circumferential direction of the rod, and wherein when any one of the at least two rods is in contact with the contact surface, the contact areas are separated in the circumferential direction by a region in which the rod and the contact surface are spaced apart, the method comprising:

inserting the shaft of the anchoring element into a bone, wherein the head of the anchoring element is in the head receiving portion of the receiving part and the locking ring is around the head receiving portion in a first position where the head can be introduced into the head receiving portion;

adjusting an angular position of the receiving part relative to the anchoring element;

selecting one of the at least two rods and inserting the rod into the channel, such that the rod contacts the contact surface of the locking ring at the at least two distinct contact areas; and advancing a fixation element into the channel to push the rod against the locking ring and to move the locking ring from the first position to a second position closer to the open end of the head receiving portion to clamp the head in the head receiving portion and to lock the angular position of the receiving part relative to the anchoring element with the locking ring.

14. The method of claim 13, wherein prior to inserting the anchoring element into the bone, the method further comprises inserting the head of the anchoring element into the head receiving portion of the receiving part when the locking ring is around the head receiving portion in the first position.

15. The method of claim 14, wherein prior to inserting the head into the head receiving portion, the method further comprises mounting the locking ring around the head receiving portion from the open end.

* * * * *

UNITED STATES PATENT AND TRADEMARK OFFICE
CERTIFICATE OF CORRECTION

PATENT NO. : 8,764,805 B2  
APPLICATION NO. : 13/336693  
DATED : July 1, 2014  
INVENTOR(S) : Lutz Biedermann et al.

Page 1 of 1

It is certified that error appears in the above-identified patent and that said Letters Patent is hereby corrected as shown below:

On the Title Page

(56) References Cited, FOREIGN PATENT DOCUMENTS

Delete "10/2009"  
Insert -- 10/2000 --

In the Specification

Column 1, line 11

Delete "EP 1.0 196 866.7"  
Insert -- EP 10 196 866.7 --

Column 2, line 44

Delete "a"  
Insert -- an --

Column 2, line 53

After "according"  
Insert -- to --

Column 2, line 60

Delete "portion"  
Insert -- a portion --

Signed and Sealed this  
Seventeenth Day of March, 2015

Michelle K. Lee  
*Director of the United States Patent and Trademark Office*